United States Patent [19]

Horecker

[11] Patent Number: 4,614,731
[45] Date of Patent: Sep. 30, 1986

[54] PEPTIDE HAVING IMMUNOPOTENTIATING ACTIVITY SIMILAR TO THYMOSIN ALPHA$_1$

[75] Inventor: Bernard L. Horecker, New York, N.Y.

[73] Assignee: Hoffmann-La Roche Inc., Nutley, N.J.

[21] Appl. No.: 742,827

[22] Filed: Jun. 10, 1985

Related U.S. Application Data

[63] Continuation of Ser. No. 532,418, Sep. 15, 1983, abandoned, which is a continuation-in-part of Ser. No. 511,821, Jul. 8, 1983, abandoned.

[51] Int. Cl.$^4$ .................. A61K 37/24; A61K 37/02; C07K 7/48
[52] U.S. Cl. ................................. 514/12; 514/21; 424/95; 530/301; 530/324; 530/837
[58] Field of Search .................. 514/12; 260/112.5 R

[56] References Cited

U.S. PATENT DOCUMENTS 4,079,127  3/1978  Goldstein et al. .................. 514/12
4,082,737  4/1978  McGregor et al. .......... 260/112.5 R
4,388,234  6/1983  Horecker .................... 260/112.5 R

OTHER PUBLICATIONS

Goldstein, Allan L. "Thymic Hormones and Lymphokines", 1984, pp. 21-35, Plenum Press.

*Primary Examiner*—Donald B. Moyer
*Assistant Examiner*—Jacqueline M. Stone
*Attorney, Agent, or Firm*—Jon S. Saxe; George M. Gould; Patricia A. Coburn

[57] ABSTRACT

A new biologically active polypeptide hormone has been isolated from calf thymosin fraction 5 and has been given the designation thymosin alpha$_{11}$. The peptide contains seven additional amino acid residues at the carboxy terminus when compared to thymosin alpha$_1$. Thymosin alpha$_{11}$ is one of several peptides present in thymosin fraction 5 which participate in the regulation, differentiation and function of thymic dependent lymphocytes (T cells). The new peptide is approxomately 16 times as potent in the protection of subject animals against opportunistic infections as thymosin fraction 5 and approximately equal in potency to thymosin alpha$_1$.

3 Claims, 2 Drawing Figures

→ FRAGMENTS DERIVED FROM COOH TERMINUS, EDMAN ANALYSIS
← FRAGMENTS DERIVED BY CARBOXYPEPTIDASE Y TREATMENT

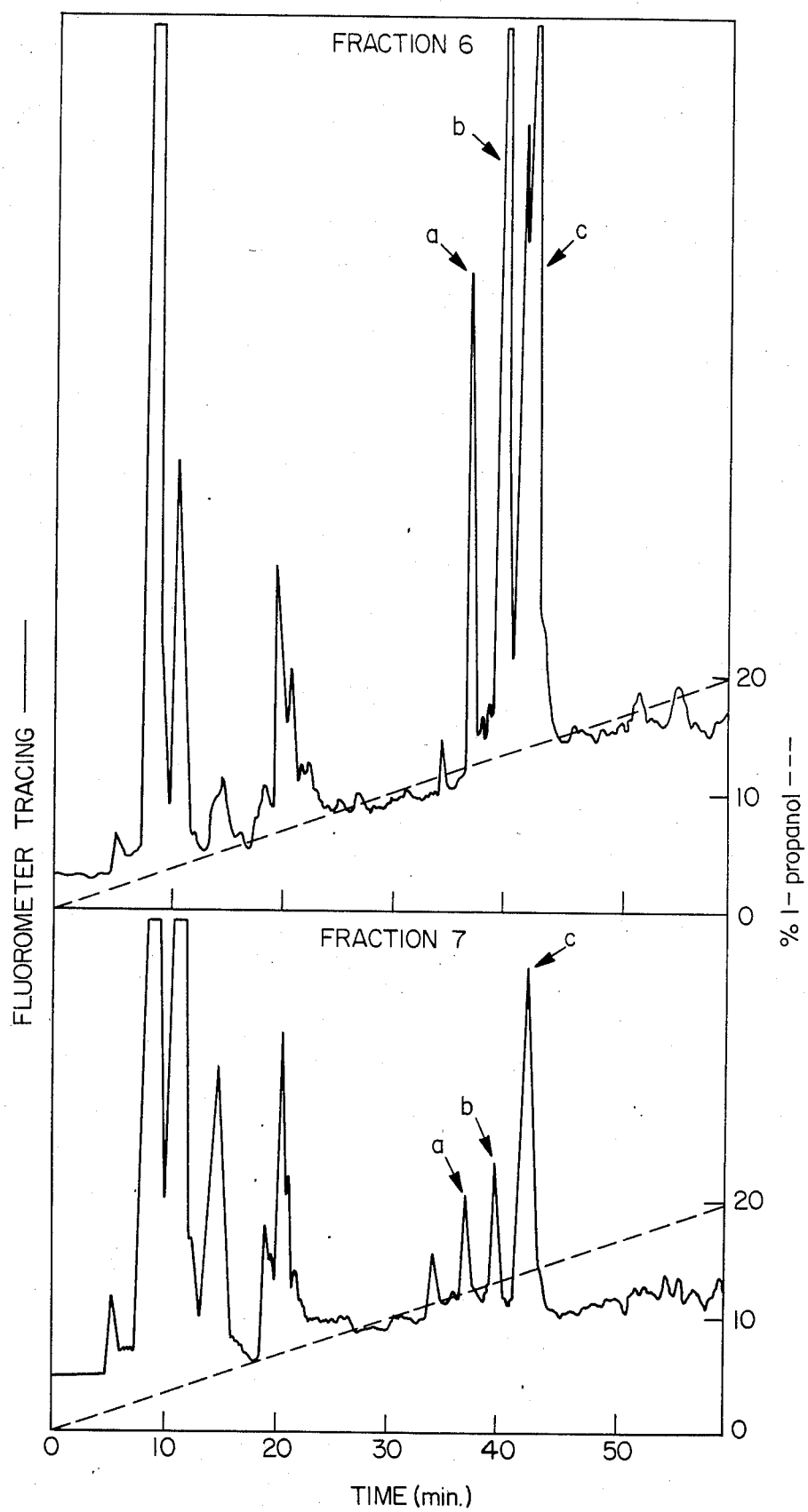

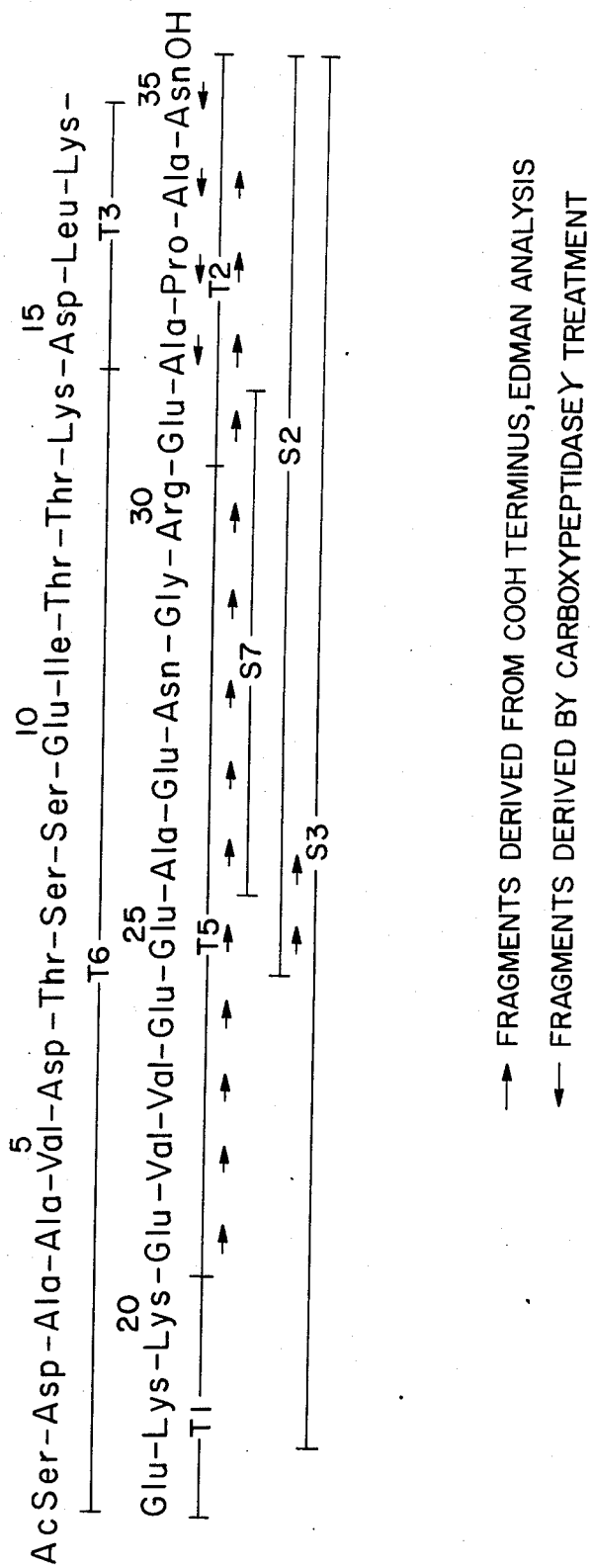

PEPTIDE HAVING IMMUNOPOTENTIATING ACTIVITY SIMILAR TO THYMOSIN ALPHA$_1$

RELATED APPLICATION

This is a continuation of application Ser. No. 532,418 filed Sept. 15, 1983, which is a continuation-in-part of Ser. No. 511,821, filed July 8, 1983, both now abandoned.

BACKGROUND OF THE INVENTION

Thymosin fraction 5, known for example from U.S. Pat. No. 4,082,737, is a potent immunopotentiating preparation and can act in lieu of the thymus gland to reconstitute immune functions in thymic deprived and/or immunodeprived individuals. Ongoing clinical trials with fraction 5 suggest that thymosin is effective in increasing T cell numbers and normalizing immune function in children with thymic dependent primary immunodeficiency disease and can increase T cell numbers in immunodepressed cancer patients.

The first active peptide isolated and characterized from thymosin fraction 5 has been termed thymosin alpha$_1$. See for example U.S. Pat. No. 4,079,127 for a description of this peptide's isolation and characterization. Synthesis of alpha$_1$ by solution and solid phase synthesis techniques is described in U.S. Pat. No. 4,148,788. Additionally the synthesis of thymosin alpha$_1$ by solution phase procedures is shown in U.S. Pat. No. 4,116,951. Thymosin alpha$_1$ has been found to be one or more orders of magnitude more active than fraction 5 in several in vitro and in vivo assay systems designed to measure T cell differentiation and function. Thymosin alpha 1 is currently in the clinic to determine its efficacy in the treatment of immunodeficiency diseases, immunodepressed cancer patients and in the prevention of opportunistic infections in immunosuppressed patients.

Thymosin alpha$_{11}$ shares the biological activities of thymosin alpha 1 and in view of its structure relationship to thymosin alpha$_1$ appears to represent a proteolytically modified fragment of the precursor native thymic peptide. However, since it is a large fragment and thus closer in structure to the native peptide it would represent a clinically preferred therapeutic substance.

DESCRIPTION OF THE INVENTION

The present invention relates to the isolation and first complete structural determination of a new polypeptide isolated from thymosin fraction 5. This peptide has been termed thymosin alpha 11. Thymosin alpha$_{11}$ has been found to have the same quantitative and qualitative biological activity as has been observed for thymosin alpha$_1$ in in vivo assay systems designed to measure T cell differentiation and function.

Thymosin alpha$_{11}$ is a peptide composed of 35 amino acid residues, the first 28 of which are identical to thymosin alpha$_1$. Thymosin alpha$_{11}$ has the following amino acid sequence:

AcSer—Asp—Ala—Ala—Val—Asp—Thr—Ser—Ser—Glu—
—Ile—Thr—Thr—Lys—Asp—Leu—Lys—Glu—Lys—Lys—
—Glu—Val—Val—Glu—Glu—Ala—Glu—Asn—Gly—
—Arg—Glu—Ala—Pro—Ala—AsnOH.

Thymosin alpha$_{11}$ was isolated from calf thymus fraction 5 by a combination of preparative isoelectric focusing (see Hannappel et al., *Proc. Natl. Acad. Sci. USA* 79, 1708–1711 (1982)) and HPLC (See Stein and Moschera, *Methods in Enzymology* 79, 7–16 (1981)).

Thymosin fraction 5 prepared in accordance with known procedures, see e.g. U.S. Pat. No. 4,079,127, was electrofocused for 17 hours at a maximum current of 20 mA and a maximum voltage of 1.1 kV, the gel bed was divided into 30 sections with a stainless steel grid and peptides in each fraction eluted with 5 ml of water. The pH of each eluate was determined with a Radiometer PHM 83 Autocal pH meter.

For analysis of isoelectric focusing fractions by HPLC, aliquots were lyophilized and dissolved in a small volume of buffer A (0.2M pyridine, 1.0M in formic acid). Elution was with buffer A and a linear gradient of 1-propanol.

In FIG. 1 results are shown for the HPLC analysis of isoelectric focusing fractions 6 and 7. Peaks a, b, and c were identified as des-(25-28)-thymosin alpha$_1$, thymosin alpha$_1$, and thymosin alpha$_{11}$ respectively. Some additional thymosin alpha$_1$ was recovered from isoelectric focusing fractions 4 and 5 and a small quantity of thymosin alpha$_{11}$ was also present in isoelectric focusing fraction 5 (data not shown).

Separation of peptides by HPLC was performed with an Ultrasphere ODS C18 column (5μ, 4.6×250 mm, Altex Scientific) with a fluorescamine detection system as described by Stein and Moschera, supra.

The run shown in FIG. 1 was derived from a 2 gram batch of calf thymosin fraction 5. The peptides in peak c of the HPLC purification step from isoelectric focusing fractions 6 and 7 were combined, lypholized and purified by rechromatography on HPLC utilizing the methodology described for FIG. 1. An aliquot (600 μg) was digested with 42.9 μg of TPCK-treated trypsin in 100 μl of 0.4M pyridine, pH 7.5. After 15 hours at 25° C. the reaction mixture was lypholized and the tryptic peptides were separated by HPLC using a gradient of acetonitrile (0 to 30 volume percent). Fractions (0.65 ml) were collected every minute. At 6-second intervals, 5 μl samples were diverted to the fluorescamine detector.

Six fragments were recovered and identified by their amino acid composition as summarized below in Table 1.

TABLE I

Amino acid composition of peptides isolated from tryptic and *S. aureus* V8 Protease digests of thymosin $\alpha_{11}$

| Residue | T1 (68)* | T2 (53)* | T3 (57)* | T4 (60)* | T5 (32)* | T6 (66)* | S2 (2.6)+ | S3 (0.8)+ | S7 (3.7)+ |
|---|---|---|---|---|---|---|---|---|---|
| Asp |  | 0.8 | 1.3 | 1.0 | 1.1 | 2.2 | 1.3 | 1.4 | 1.4 |
| Thr |  |  |  |  |  | 2.7 |  |  |  |
| Ser |  |  |  |  |  | 2.7 |  |  |  |
| Glu | 1.0 | 1.0 |  | 3.4 | 3.3 | 1.1 | 2.4 | 4.8 | 1.7 |
| Gly |  |  |  | 1.0 | 1.0 |  | 1.4 | 1.1 | 1.9 |
| Ala |  | 2.0 |  | 1.0 | 1.0 | 1.9 | 2.6 | 2.7 | 1.0 |

TABLE I-continued

Amino acid composition of peptides isolated from tryptic and *S. aureus* V8 Protease digests of thymosin $\alpha_{11}$

| Residue | T1 (68)* | T2 (53)* | T3 (57)* | T4 (60)* | T5 (32)* | T6 (66)* | S2 (2.6)+ | S3 (0.8)+ | S7 (3.7)+ |
|---|---|---|---|---|---|---|---|---|---|
| Val |  |  |  | 1.9 | 1.5 | 1.1 |  | 1.0 |  |
| Ile |  |  |  |  |  | 1.0 |  |  |  |
| Leu |  |  | 0.8 |  |  |  |  |  |  |
| Lys | 2.1 |  | 1.0 | 0.2 |  | 1.0 |  | 2.9 |  |
| Arg |  |  |  | 1.0 | 1.1 |  | 1.0 | 1.0 | 0.5 |
| Pro |  | 1.3 |  |  |  |  | nd** | nd** | nd** |

Calculated based on assigning a value of 1.0 for the residue as underlined.
*Nanomoles recovered from a digest of 200 nanomoles of thymosin $\alpha_{11}$.
+Nanomoles recovered from a digest of 8.7 nanomoles of thymosin $\alpha_{11}$.
**Not determined.

Peptides T6, T3 and T1 were identical to peptides derived from residues 1–14, 15–17 and 18–20, respectively, of thymosin alpha$_1$. Peptides T4 and T5 were similar in amino acid composition, differing only in the presence of lysine in peptide T4. Their composition indicated that they corresponded to residues 20–28 of thymosin alpha$_1$, plus glycine and arginine. Since peptide T5 did not contain lysine, it was concluded that arginine must be located at the COOH terminus of the peptide (See FIG. 2). The tryptic digest contained an additional peptide (T2) which was not present in tryptic digests of thymosin alpha$_1$. This new peptide contained no lysine or arginine, and must therefore have arisen from the COOH-terminus of thymosin alpha$_{11}$.

Edmann degradation of tryptic peptide T2 yielded the sequence Glu-Ala-Pro-Ala-Asn-OH. This data is summarized in Table 2.

quantities of two of the fragments, whose amino acid composition corresponded to residues 19–35 (peptide S3) and 25–35 (peptide S2) of thymosin alpha$_{11}$ were also isolated from the *S. aureus* Protease digests (Table 1 and FIG. 2). The results establish thymosin alpha$_{11}$ as containing the thymosin alpha$_1$ sequence plus seven additional amino acids at the COOH-terminus.

The biological activity of thymosin alpha$_1$ can be determined by utilizing in vivo assays known in the art. Thus, for example, inbred strains of mice are known to vary in their susceptability to infection with *C. albicans*. Thus, mice of such strains as C$_3$H/HeJ or CBA/CaJ are highly susceptible to infection, whereas mice of such strains as C$_{57}$Bl/10SNJ or C$_{57}$Bl/KsJ were highly resistant to challenge. Since resistance to infection with *C. albicans* is associated with cell-mediated processes, and therefore with T-lymphocytes, thymic hormones

TABLE 2

Edman degradation of tryptic peptide T2

| Step | Nanomoles of peptide recovered after each step of degradation | Subtractive method, amino acid composition of residual peptides* | | | | | Recovered after hydrolysis of the anilinothiazolinone(nmol)# | PTH amino acid identified |
|---|---|---|---|---|---|---|---|---|
| | | Glx | Ala | Pro | Ala | Asx | | |
| 0 | (35.3)** | 1.3 | 1.2 | 1.7 | 1.2 | 1.0 |  |  |
| 1 | 28.8+ | 0.1 | 1.1 | 1.4 | 1.1 | 1.0 | Glu (6.9) | Glu |
| 2 | 30.6+ | 0.2 | 0.1 | 1.1 | 1.2 | 1.0 | Ala (5.9) | Ala |
| 3 | 36.7+ | 0.4 | 0 | 0.6 | 1.2 | 1.0 | Pro (2.6) | Pro |
| 4 | 30.3+ | 0.3 | 0 | nd | 0.4 | 1.0 | Ala (2.8) | Ala |

*Amino acid compositions of an aliquot of thymosin $\alpha_{11}$ or of aliquots from the aqueous phase after each step of Edman degradation. The results are presented as ratios to the quantity of aspartic acid. Half the total for alanine was arbitrarily assigned to each alanine residue in the sequence for the first 2 steps.
An aliquot for each anilinothiazolinone was removed before cyclization and hydrolyzed for amino acid analysis.
The PTH amino acids obtained at each step of the degradation were identified by HPLC.
**This quantity was used for the degradation procedure.
+Estimated from the results of amino acid analysis after acid hydrolysis.

Asparagine was recovered as the free amino acid after the fourth step of the Edman procedure. Localization of peptide T2 at the COOH terminus of thymosin alpha$_{11}$ was confirmed by digestion of the later with carboxypeptidase (Y) which released approximately one equivalent of asparagine, followed by alanine (2 equivalents) and proline (one equivalent). The location of arginine at position 30 was confirmed by the isolation of a major fragment containing arginine after digestion of thymosin alpha$_{11}$ with *S. aureus* V8 protease (peptide S7 Table 1). The amino acid composition of this peptide corresponded to that predicted for residues 26–31 of thymosin alpha$_{11}$ including the last four residues of thymosin alpha$_1$, plus the first three amino acid residues, glycine, arginine and glutamic acid, found in the COOH-terminal extension of thymosin alpha$_{11}$. Smaller should have an effect on the host response. Thymosin fraction 5 and some peptides derived therefrom have been found to enhance maturation and replication of T-lymphocytes (Goldstein et al., Rec. Progress in Hormone Research 37, 369–415 (1981)) and accordingly should influence of the resistance of a susceptible murine strain, such as C$_3$H/HeJ, to infection with *C. albicans*.

Thymosin fraction$_5$, alpha$_1$, or alpha$_{11}$ was injected daily i.p. in graded doses into three different groups of mice, beginning two days before intravenous challenge with $4 \times 10^4$ cells of *C. albicans*. In comparison with control mice, all three thymic derivatives provided protection. The results are summarized in Table 3 below.

TABLE 3

Effect of thymosin fraction 5 and thymic peptides on the growth of *Candida albicans* in C₃H/HeJ mice

| Thymosin fraction 5 | | Thymosin $\alpha_1$ | | Thymosin $\alpha_{11}$ | |
|---|---|---|---|---|---|
| Dose ng/mouse | *C. albicans* cell count* | Dose ng/mouse | *C. albicans* cell count* | Dose ng/mouse | *C. albicans* cell count* |
| 2560 | 8500 | 80 | 5870 | 80 | 4200 |
| 5120 | 440 | 160 | 190 | 160 | 510 |
| 10240 | 320 | 320 | 780 | 320 | 320 |
| 20480 | 1600 | 640 | 1410 | 640 | 1260 |

Mice were treated daily with the indicated doses of thymosin fraction 5, thymosin $\alpha_1$ or thymosin $\alpha_{11}$ and challenged with $4 \times 10^4$ cells of *C. albicans* two days after the start of treatment
*Three mice from each set were sacrificed on days 7, 14 and 21 after infection and the values represent the average number of organisms in the left kidneys of the nine mice in each set.

The polypeptides, thymosin alpha₁, and thymosin alpha₁₁, were approximately equal in potency, being most active in daily doses of 160-320 ng per mouse i.p. Since the optimum dose for fraction 5 was 5-10 μg, the peptides were therefore about 30 times more potent than fraction 5 in their ability to induce resistance to infection with *C. albicans*.

Thus, thymosin alpha₁₁, in analogy to thymosin alpha₁, may be administered to warm-blooded mammals by parenteral application either intravenously, subcutaneously or intramuscularly. The compound is a potent immunopotentiating agent with a daily dosage in the range of about 1 to 100 μg/kg of body weight per day for intravenous administration. Obviously the required dosage will vary with the particular condition being treated, the severity of the condition and duration of the treatment. A suitable dosage form for pharmaceutical use is 1 mg of lypholized thymosin alpha₁₁ per vial to be reconstituted prior to use by the addition of sterile water or saline.

Also included within the scope of the present invention are the pharmaceutically acceptable salts of thymosin alpha₁₁ such as the sodium or potassium salts or of strong organic bases such as guanidine. In addition, the counter ions of these cations as well as of lysine residues in thymosin alpha₁₁, such as the hydrochloride, hydrobromide, sulphate, phosphate, maleate, acetate, citrate, benzoate, succininate, ascorbate and the like, may be included in the preparation.

It is also within the scope of the present invention to modify the sequence of thymosin alpha₁₁ by single amino acid changes or by derivatizing the carboxy terminus by ester or amide formation. Also within the scope of the invention is the unblocked amino terminus analog desacetyl thymosin alpha₁₁ which can be produced directly by the use of recombinant DNA techniques by employing a synthetic gene derived by applying the genetic code to the known sequence of the peptide. The desacetylthymosin alpha₁₁ would have the same biological activity as thymosin alpha₁₁ by analogy to the relationship between thymosin alpha₁ and desacetylthymosin alpha₁.

I claim:

1. A peptide of the sequence:

AcSer—Asp—Ala—Ala—Val—Asp—Thr—Ser—Ser—Glu—
—Ile—Thr—Thr—Lys—Asp—Leu—Lys—Glu—Lys—Lys—
—Glu—Val—Val—Glu—Glu—Ala—Glu—Asn—Gly—
—Arg—Glu—Ala—Pro—Ala—AsnOH and the pharmaceutically acceptable acid and base addition salts thereof.

2. A method for reconstituting immune functions in thymic deprived or immunodeprived warm-blooded animals which method comprises parenterally administering to such mammal an immunopotentiating effective amount of a peptide having the sequence:

AcSer—Asp—Ala—Ala—Val—Asp—Thr—Ser—Ser—Glu—
—Ile—Thr—Thr—Lys—Asp—Leu—Lys—Glu—Lys—Lys—
—Glu—Val—Val—Glu—Glu—Ala—Glu—Asn—Gly—
—Arg—Glu—Ala—Pro—Ala—AsnOH or the pharmaceutically acceptable acid and base addition salts thereof.

3. The method of claim 2 wherein a daily dosage in the range of from about 1 to 100 μg/kg of body weight per day is administered.

* * * * *